(12) United States Patent
Ohnishi et al.

(10) Patent No.: US 8,785,348 B2
(45) Date of Patent: Jul. 22, 2014

(54) METHOD OF PREPARING CARRIER TO SEPARATE NUCLEIC ACIDS, CARRIER AND MICRO CHANNEL TO SEPARATE NUCLEIC ACIDS, AND METHOD AND APPARATUS FOR SEPARATING NUCLEIC ACIDS

(75) Inventors: Michihiro Ohnishi, Kanagawa (JP); Noriyuki Kishii, Kanagawa (JP); Takuya Kishimoto, Tokyo (JP); Naoyuki Sasaki, Tokyo (JP); Hidetoshi Watanabe, Chiba (JP)

(73) Assignee: Sony Corporation, Tokyo (JP)

( * ) Notice: Subject to any disclaimer, the term of this patent is extended or adjusted under 35 U.S.C. 154(b) by 667 days.

(21) Appl. No.: 12/432,078

(22) Filed: Apr. 29, 2009

(65) Prior Publication Data

US 2009/0275743 A1 Nov. 5, 2009

(30) Foreign Application Priority Data

May 2, 2008 (JP) ................ 2008-120166

(51) Int. Cl.
*B01J 20/00* (2006.01)
*B01J 23/02* (2006.01)
*C07H 21/00* (2006.01)

(52) U.S. Cl.
USPC ........ 502/407; 502/439; 536/25.4; 536/25.42

(58) Field of Classification Search
None
See application file for complete search history.

(56) References Cited

U.S. PATENT DOCUMENTS

| | | | |
|---|---|---|---|
| 4,849,513 A * | 7/1989 | Smith et al. | 536/26.6 |
| 5,648,480 A * | 7/1997 | Letsinger et al. | 536/25.34 |
| 7,419,817 B2 * | 9/2008 | Chiorini et al. | 435/239 |

FOREIGN PATENT DOCUMENTS

| | | |
|---|---|---|
| JP | 2003-125764 A | 5/2003 |
| JP | 2004-121226 A | 4/2004 |
| JP | 2005-130795 A | 5/2005 |
| JP | 2007-309900 A | 11/2007 |

OTHER PUBLICATIONS

Nicholls et al., "Nucleic Acid Analysis by Sandwich Hybridization," Journal of Clinical Laboratory Analysis, 3, 122-135 (1989).*

* cited by examiner

*Primary Examiner* — Lawrence E Crane
(74) *Attorney, Agent, or Firm* — Wolf, Greenfield & Sacks, P.C.

(57) ABSTRACT

The present disclosure relates to a method and apparatus for separating nucleic acids. A carrier may include a porous microbead having cation-exchangeable groups attached to the surface of the porous microbead. Capturing chains modified with positively charged functional groups and having a base sequence complementary to a target nucleic acid chain sequence are immobilized on to the surface of the porous microbead. In various embodiments, capturing chains are immobilized on to the surface of the porous microbead through an ion exchange bond or a covalent bond with the cation-exchangeable groups of the porous microbead. In some cases, the porous microbead has a number of through pores adapted to permit a solution to pass rapidly through the through pores and a number of diffusive pores adapted to permit a solute of the solution to diffuse into the diffusive pores. A solution having a target nucleic acid chain corresponding to the target nucleic acid chain sequence of the capturing chains may be passed through a channel that is packed with porous microbeads so as to result in hybridization of the capturing chain and the target nucleic acid chain. The porous microbeads may be structured such that the pressure in the channel upon passing of the solution through the channel does not build significantly.

8 Claims, 4 Drawing Sheets

METHOD OF PREPARING CARRIER TO SEPARATE NUCLEIC ACIDS, CARRIER AND MICRO CHANNEL TO SEPARATE NUCLEIC ACIDS, AND METHOD AND APPARATUS FOR SEPARATING NUCLEIC ACIDS

CROSS REFERENCE TO RELATED APPLICATION

The present application claims priority under 35 U.S.C. §119 to Japanese Patent Application No. JP 2008-120166 filed in the Japanese Patent Office on May 2, 2008, the entire contents of which is incorporated herein by reference.

BACKGROUND OF THE INVENTION

1. Field of the Invention

The present invention relates to a method of preparing a carrier to separate nucleic acids, a carrier and micro channel to separate nucleic acids, and a method and apparatus of separating nucleic acids. More particularly, the present invention relates to a method of preparing a cation-exchangeable porous carrier to separate nucleic acids.

2. Description of the Related Art

Recent years have seen a remarkable development in bioassay technologies applicable to gene mutation analysis, single nucleotide polymorphism (SNPs) analysis, gene expression frequency analysis, and gene network elucidation. Such technologies employ integrated substrates called DNA (Deoxyribonucleic Acid) chips or DNA microarrays (which will be collectively referred to as DNA chips hereinafter).

The sensor chip technology that employs DNA chips and protein chips (with proteins integrated thereon) is designed to separate and detect a target substance in a sample and determine its content with the help of specific interactions between a target substance and a detecting substance.

There has recently been proposed a new technology that employs a fluid channel or capillary for interactions between a target substance and a detecting substance. The interaction between substances is applied to a new technology that causes the hybridization reaction of nucleic acids to take place in a fluid channel or capillary. For example, Japanese Patent Laid-open No. 2005-130795 (hereinafter referred to as Patent Document 1) discloses an apparatus for analysis of polynucleotide which includes a section for amplification of polynucleotide and a section for hybridization which has a porous layer to which is fixed a detecting oligonucleotide, with the sections being connected to each other through a fluid channel. Also, Japanese Patent Laid-open No. 2004-121226 (hereinafter referred to as Patent Document 2) discloses a method of analyzing polynucleotide by allowing hybridization to take place between a probe compound (fixed to the inside of a capillary fluid channel) and a target polynucleotide.

The interaction between substances that takes place in a thin fluid channel such as capillary poses a problem with a significant pressure rise in the channel which results from flowing sample solutions. In the case where a nucleic acid chain is the target substance, it forms a hybrid in the thin fluid channel to reduce the substantial volume of the channel and increases the pressure in the channel. Moreover, nucleic acid chains other than target nucleic acid chains may adsorb nonspecifically to the inside of the channel to clog the channel and increase the pressure in the channel.

The increased pressure in the channel causes solutions to leak out from joints and any other weak parts. Loss of solutions due to leakage reduces the amount and concentration of reaction substances, which would prevent the expected interactions between substances. Moreover, leakage could endanger safety if the sample solution contains hazardous materials.

To cope with the foregoing situation, the present inventors have proposed a micro fluid channel which is free from clogging and pressure increase, as disclosed in Japanese Patent Laid-open No. 2007-309900 (hereinafter referred to as Patent Document 3). This micro fluid is made up of two sections. The first one is filled with beads for hybrid formation. The second one is placed in the downstream region of the first one (or the hybrid forming section) so that it permits solutions to flow rapidly.

SUMMARY OF THE INVENTION

Patent Document 3 discloses a micro fluid channel provided with a section which permits fluids to flow rapidly. This section is filled with perfusion chromatography particles. Typical of such particles are porous carriers having large pores (called through pores) and small pores (called diffusive pores). The particles of porous carriers permit the solute in a sample solution to diffuse into all the diffusive pores and also permits the sample solution itself to pass through the through pores. Therefore, the micro fluid channel, which includes a hybrid forming section for nucleic acids to undergo hybridization therein and a fluid flow accelerating section filled with perfusion chromatography particles (which is placed downstream the hybrid forming section), prevents the internal pressure from rising in the fluid channel and permits the sample solution to flow rapidly through the fluid channel.

It is desirable for the present invention to provide a new technology useful for hybridization of nucleic acids in the foregoing micro fluid channel, the technology being intended to prevent the internal pressure from rising in the channel, preventing sample solutions from leaking from the channel, and raising the flow rate of sample solutions.

The first embodiment of the present invention resides in a method for producing a carrier for nucleic acid separation, the method including a step of immobilizing capturing chains onto a porous carrier having cation-exchangeable groups thereon by ion exchange bonding, the capturing chains having a base sequence complementary to target nucleic acid chains and being modified with functional groups having positive charges.

The porous carrier having cation-exchangeable groups prevent the nonspecific adsorption of nucleic acid chains to the carrier surface on account of the electric repulsion that results from negative charges due to the cation-exchangeable groups and negative charges due to phosphoric acid groups in nucleic acid chains.

Also, the porous carrier permits sample solutions to pass through rapidly.

The carrier for nucleic acid separation can be produced easily by immobilizing capturing chains to the cation-exchangeable groups on the carrier surface by ion exchange bonding.

In production of the carrier for nucleic acid separation, immobilization by ion exchange bonding is accomplished by allowing the capturing chains to come into contact with the porous carrier in a solution in which the cation concentration is high enough for the cation exchangeable groups to undergo ion exchange bonding. This is the way in which the functional groups modifying the capturing chains bind by ion exchange to the cation-exchangeable groups on the carrier surface.

Covalent bond is another way of binding the capturing chains to the cation-exchangeable groups. This ensures immobilization of capturing chains to the carrier surface.

The second embodiment of the present invention resides in a carrier for nucleic acid separation which includes a porous carrier having cation-exchangeable groups thereon and capturing chains immobilized thereto through ion exchange bond which have a base sequence complementary to target nucleic acid chains and are modified with functional groups having positive charges.

The third embodiment of the present invention resides in a carrier for nucleic acid separation which is prepared by immobilizing through ion exchange bond capturing chains, which have a base sequence complementary to target nucleic acid chains and are modified with functional groups having positive charges, to a porous carrier having cation-exchangeable groups thereon, and subsequently binding the cation-exchangeable groups and the capturing chains together through covalent bond.

The fourth embodiment of the present invention resides in a micro fluid channel which is packed with the carrier for nucleic acid separation.

The fifth embodiment of the present invention resides in a method for nucleic acid separation which includes a step of immobilizing through ion exchange bond capturing chains, which have a base sequence complementary to target nucleic acid chains and are modified with functional groups having positive charges, to a porous carrier having cation-exchangeable groups thereon.

The sixth embodiment of the present invention resides in an apparatus for nucleic acid separation which is prepared by immobilizing through ion exchange bond capturing chains, which have a base sequence complementary to target nucleic acid chains and are modified with functional groups having positive charges, to a porous carrier having cation-exchangeable groups thereon.

The preferred embodiments of the present invention provide a new technology to prevent the internal pressure from rising in the micro fluid channel for nucleic acid hybridization, preventing sample solutions from leaking from the channel, and raising the flow rate of sample solutions.

DETAILED DESCRIPTION OF THE PREFERRED EMBODIMENTS

Preferred embodiments of the present invention will be described with reference to the accompanying drawings. They merely represent some typical ones and they should not be construed to restrict the scope of the present invention.

Figure 1:
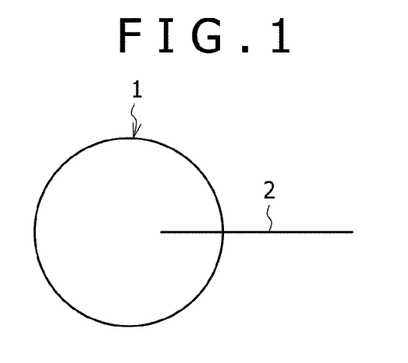
FIG. 1 is a schematic diagram showing one example of the carrier for nucleic acid separation which supports a substance thereon according to an embodiment of the present invention.

The carrier for nucleic acid separation according to an embodiment of the present invention is composed of micro beads and a substance supported thereon as schematically shown in FIG. 1.

The micro beads 1 are porous beads having cation-exchangeable groups attached to the surface thereof. The cation-exchangeable groups include carboxyl groups, sulfonyl groups, sulfonylmethyl groups, sulfoethyl groups, phenolic hydroxyl groups, and nitro groups. They may be used alone or in combination with one another.

Introduction of cation-exchangeable groups may be accomplished by causing cation-exchangeable groups directly bounded to functional groups on the surface of the micro beads 1. To be specific, the micro beads 1 are treated with chloroacetic acid which combines with hydroxyl groups thereon, so that carboxylic acid is introduced. Alternatively, the micro beads 1 are treated with an adequate compound which combines with hydroxyl groups thereon, so that epoxy groups or allyl groups are introduced and they are subsequently sulfonized.

On the surface of the micro beads 1 are immobilized the capturing chains 2 which capture target nucleic acid chains to be separated. According to an embodiment of the present invention, the target nucleic acid chains include not only DNA and RNA (Ribonucleic Acid) but also nucleic acid analogs such as LNA (Locked Nucleic Acid) which are obtained by modifying the structure of the ribose portion of DNA and RNA. The capturing chains 2 may be selected from DNA and RNA and their analogs according to the kind of target nucleic acid chains.

The capturing chains 2 have a base sequence complementary to the target nucleic acid chains and are highly compatible with them, so that their mutual reaction forms double strands (or hybrid). The base sequence of the capturing chain 2 may have any length (or any number of bases); it is not specifically limited in the number of bases so long as it has a base sequence complementary to at least one portion of the base sequence of the target nucleic acid chains. Usually, the capturing chains 2 should have several bases to several hundreds of bases, preferably about ten bases to about one hundred bases.

It is not always necessary that the capturing chains 2 have a base sequence completely complementary to the target nucleic acid chains. The capturing chains 2 may have one or more mismatches (noncomplementary bases) in their base sequence so long as they form double strands (for hybridization) with the target nucleic acid chains.

The capturing chains 2 may be immobilized to the surface of the micro beads 1 by ion exchange between the capturing chains 2 and the cation exchangeable groups on the surface of the beads. For the ion exchange bonding, the capturing chains 2 are modified with functional groups having positive charges, such as amino groups, imide groups, and ammonium groups. The capturing chains 2 are modified with functional groups by chemically attaching an amino group to the 5' end of the base sequence. The capturing chains 2 bind to the surface of the beads through the ion exchange reaction between the positive charges of the amino group or the like and the negative charges of the cation exchangeable groups on the surface of the beads.

Usually, the beads for nucleic acid separation have the capturing chains immobilized thereto through avidin-biotin bond or coupling reaction (such as diazo coupling reaction). The avidin-biotin bond is formed between streptavidin immobilized to the bead surface and biotin attached to the 5' end of the capturing chains.

The micro beads 1, however, have the capturing chains 2 immobilized through ion exchange bond with the cation exchangeable groups on the bead surface. The carrier with cation-exchangeable groups introduced onto its surface prevents nonspecific adsorption of nucleic acid chains on account of their electric repulsion toward negative charges of phosphoric acid groups in nucleic acid chains. Another embodiment of the present invention to provide the carrier for nucleic acid separation and the method for producing the carrier is easily achieved if the capturing chains are modified with functional groups having positive charges and immobilized onto the surface of the carrier having cation-exchangeable groups introduced onto the surface thereof.

Immobilization of the capturing chains 2 onto the surface of the micro beads may be accomplished by ion exchange reaction (for covalent bond) of the capturing chains 2 with the cation-exchangeable groups on the bead surface. Covalent bond between the capturing chain 2 and the cation-exchangeable group may result from condensation reaction (such as condensation accompanied by removal of ethanol). Covalent bond allows the capturing chains 2 to be immobilized to the cation-exchangeable groups on the bead surface more firmly than ion exchange bond.

Figure 2:
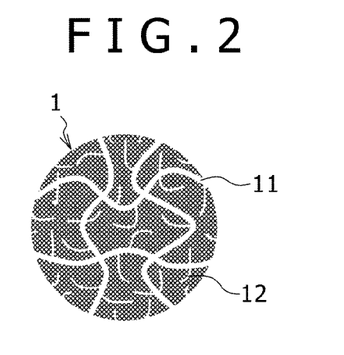
FIG. 2 is a schematic sectional view showing one example of the structure of micro bead.

The micro bead 1 has the structure as shown in FIG. 2 which is a schematic sectional view.

The micro bead 1 is a porous one. Such porous beads are exemplified by perfusion chromatography particles. The micro bead 1 has through pores 11 (which are large) and diffusive pores (which are small), as indicated by arrows. Because of this internal structure, the micro bead 1 allows the sample solution to pass rapidly through the through pores 11 and also allows the solute in the sample solution to diffuse into the diffusive pores 12.

Figure 3:
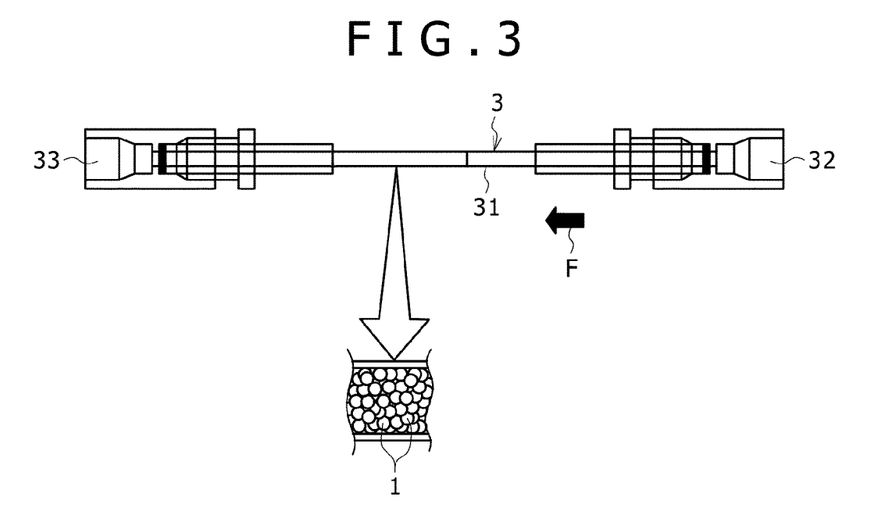
FIG. 3 is a diagram showing a preferred embodiment of the micro fluid channel according to another embodiment of the present invention.

Shown in FIG. 3 is the micro fluid channel according to a preferred embodiment of the present invention.

The micro fluid channel 3 shown in FIG. 3 is composed of a narrow tube 31 through which the sample solution flows, an inlet 32 attached to one end of the narrow tube 31, and an outlet 33 attached to the other end of the narrow tube 31. The sample solution flows in the direction indicated by the arrow F.

The micro fluid channel 3 has the narrow tube 31 packed with the micro beads 1. Before being packed into the narrow tube 31, the micro beads 1 have the capturing chains 2 immobilized onto the surface thereof through ion exchange bond or covalent bond with the cation exchangeable groups attached thereto.

Alternatively, the micro beads 1 are packed into the micro fluid channel 3 and then the capturing chains 2 are immobilized onto their surface according to the following procedure. First, the porous beads with cation exchangeable groups introduced onto their surface are packed into the narrow tube 31. A solution of the capturing chains 2 modified with functional groups having positive charges is passed through the narrow tube 31 from the inlet 32. Prior to this step, the beads may be conditioned with a buffer solution flowing through the narrow tube 31.

The solution of the capturing chains 2, which has been fed to the narrow tube 31, passes through the through holes 11 in the porous beads and leaves the outlet 33. During this process, the capturing chains 2 in the solution spread into every corner of the diffusive pores 12 where they undergo ion exchange reaction with the cation-exchangeable groups which have been introduced onto the bead surface, so that they are immobilized onto the bead surface through ion exchange bond.

The solution of the capturing chains 2 to be fed to the narrow tube 31 should have an adequate concentration dilute enough for the capturing chains 2 (modified with functional groups having positive charges) not to impede the ion exchange reaction with the cation-exchangeable groups on the bead surface. A solution containing the capturing chains 2 in high concentration is detrimental to ion exchange reaction between the cation-exchangeable groups on the bead surface and the functional groups that modify the capturing chains 2. This results in the capturing chains 2 remaining not immobilized.

The solution concentration of the capturing chains 2 should be properly established according to the type of the cation-exchangeable groups on the bead surface, the type of the functional groups that modify the capturing chains 2, and the strength of the ion exchange bond, so as to ensure bonding. It is desirable to dissolve the capturing chains 2 in pure water to ensure firm ion exchange bonding between the cation-exchangeable groups on the bead surface and the functional groups that modify the capturing chains 2.

The covalent bond between the cation-exchangeable groups on the bead surface and the functional groups that modify the capturing chains 2 may be achieved by condensation reaction (such as the one accompanied by removal of ethanol) under conditions for the ion exchange bond to take place.

The foregoing procedure permits ion exchange bonding or covalent bonding to take place in the micro fluid channel 3 between the capturing chains 2 and the cation ex-changeable groups on the bead surface.

Figure 4A:
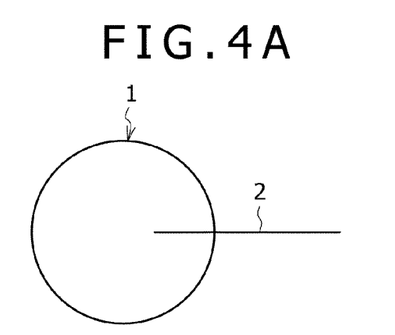
FIG. 4A to 4C are schematic diagrams showing the micro beads which vary in the substance supported thereon from one step to another in the procedure of nucleic acid separation by the micro fluid channel.
Figure 4B:
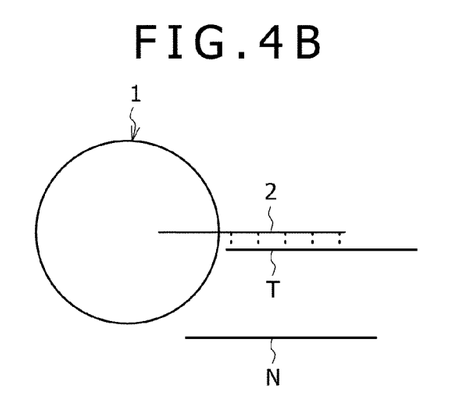
Figure 4C:
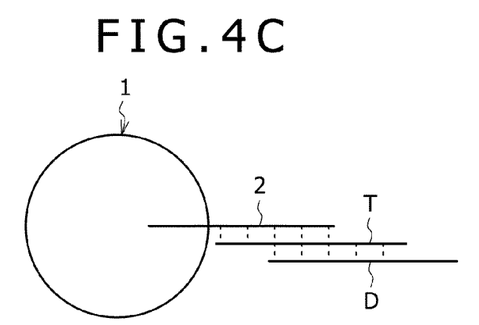

Below is described with reference to FIGS. 3 to 4C a preferred embodiment for the method of separating nucleic acids by means of the micro fluid channel 3. FIGS. 4A to 4C are schematic diagrams showing how the substances vary on the surfaces of the micro beads as the steps for nucleic acid separation proceed. An example of detection of target nucleic acid chains by sandwich hybrid method will be described here.

<Step 1>

First, the narrow tube 31 is packed with porous beads having cation-exchangeable groups introduced onto their surface. Then, it is fed with a buffer solution through the inlet 32 so that the beads undergo conditioning. Subsequently, it is fed, through the inlet 32, with a solution of the capturing chains 2 modified with functional groups having positive charges, so that ion exchange reaction takes place between the cation-exchangeable groups on the bead surface and the functional groups that modify the capturing chains 2, and the capturing chains 2 are immobilized onto the bead surface. Step 1 gives rise to the micro beads 1 which have the substance thereon as shown in FIG. 4A.

Incidentally, Step 1 may be carried out in such a way that the ion exchange reaction between the cation-exchange-able groups on the bead surface and the functional groups that modify the capturing chains 2 is replaced by condensation reaction that leads to covalent bonding.

<Step 2>

The narrow tube 31 is fed through the inlet 32 with a sample solution containing the target nucleic acid chains, so that the capturing chains 2, which have a base sequence complementary to the target nucleic acid chains, and the target nucleic acid chains form double strands (to achieve hybridization). Thus the target nucleic acid chains are captured onto the bead surface. Hybridization between the capturing chains 2 and the target nucleic acid chains is accomplished under adequate conditions, such as the temperature of the micro fluid channel and the composition of the sample solution. Step 2 gives rise to the micro beads 1 which have the substances thereon as shown in FIG. 4B. The symbols T and N in FIG. 4B denote respectively the target nucleic acid contained in the sample solution and other nucleic acids than the target nucleic acid chains.

The capturing chains 2 firmly immobilized onto the bead surface by covalent bonding securely capture the target nucleic acid chains T under any hybridization conditions (such as high concentration and high temperature).

<Step 3>

The narrow tube 31 is fed through the inlet 32 with a buffer solution to clean the beads, with the conditions for hybridization maintained. After cleaning, the narrow tube 31 is fed through the inlet 32 with the detecting chains for detection of the target nucleic acid chains T captured on the bead surface.

The detecting chains, like the capturing chains 2, have a base sequence complementary to the target nucleic acid chains T, so that the detecting chains and the target nucleic acid chains T form a hybrid through mutual reaction on account of their high affinity. The detecting chains are selected from DNA, RNA, and nucleic acid analogs according to the kind of the target nucleic acid chains T, and the length of the base sequence (or the number of bases) may be established as required. The detecting chains are not necessarily required to have a base sequence which is completely complementary to the target nucleic acid chains T, as in the case of the capturing chains 2.

The detecting chains are labeled with a fluorescent substance or a radioactive substance, so that the target nucleic acid chains T are detected by detecting fluorescence or radiation emitted from the labeling substance.

When the solution of the detecting chains is fed to the narrow tube 31 through the inlet 32, the detecting chains hybridize with the target nucleic acid chains T which hybridize the capturing chains 2. Thus, the target nucleic acid chains T form a hybrid with the capturing chains 2 and the detecting chains. (The resulting hybrid is a sandwich hybrid or a double hybrid.) The hybridization reaction between the target nucleic acid chains T and the detecting chains is accomplished under adequate conditions, such as the temperature of the micro fluid channel and the composition of the sample solution. Step 3 gives rise to the micro beads 1 which have the substances thereon as shown in FIG. 4C. The symbol D in FIG. 4C denotes the detecting chains.

The capturing chains 2 firmly immobilized onto the bead surface by covalent bonding securely capture the double hybrid composed of the target nucleic acid chains T and the detecting chains D in the second stage of hybridization.

<Step 4>

The narrow tube 31 is fed through the inlet 32 with a buffer solution to clean the beads, with the double hybrid of the target nucleic acid chains T remaining. After cleaning, the target nucleic acid chains T, which have been captured to the bead surface, are detected with the help of fluorescence or radiation being emitted from the fluorescent substance or radioactive substance with which the detecting chains D are labeled.

To be specific, the capturing chains 2 are those which have the poly(dT) sequence or poly(dU) sequence complementary to the poly(A). They capture the messenger RNA (mRNA) of eukaryotes and the target mRNA (target nucleic acid chains T) is detected by the detecting chains D having a base sequence complementary to them. The fluorescence or radiation from the detecting chains D is examined for intensity, so that the target mRNA is quantitatively determined according to the thus measured intensity. Incidentally, the capturing chains 2 may be poly(T) or poly(U) which is an RNA so long as they are complementary to poly(A) sequence.

As mentioned above, the method for separation of nucleic acids offers the following advantages. In Step 1, the capturing chains 2 are immobilized by ion exchange bonding to the cation exchangeable groups attached to the surface of porous beads packed into the micro fluid channel 3. In this way it is possible to easily prepare the micro beads 1 and the micro fluid channel 3 filled with them.

The micro beads 1 with porous structure permit the solution of capturing chains 2 and the sample solution to rapidly pass through the narrow tube 31 and to discharge from the outlet 33 in the steps 1 to 4. While the solutions are passing through the narrow tube 31, the capturing chains 2, the target nucleic acid chains T, and the detecting chains D infiltrate into every part of the diffusive pores 12. Therefore, this method for nucleic acid separation permits the solutions to pass through the narrow tube 31 at a high flow rate without increase in internal pressure. It also permits the capturing chains 2, the target nucleic acid chains T, and the detecting chains D (contained in the solution passing through the narrow tube 31) to penetrate into every part of the diffusive pores 12 of the micro beads 1, so that it contributes to efficient immobilization of the capturing chains 2 to the bead surface and efficient hybridization for the capturing chains 2, the target nucleic acid chains T, and the detecting chains D.

In addition, the micro beads 1 prevent nonspecific adsorption of nucleic acid chains to the bead surface because of electric repulsion between negative charges of the cation exchangeable groups introduced onto the bead surface and negative charges of phosphoric acid groups of nucleic acids. This in turn prevents the internal pressure from increasing due to nonspecific adsorption of the capturing chains 2 to the bead surface. This leads to a decrease in fluorescence and radiation (as noise signals) resulting from nonspecific adsorption that occurs when the target nucleic acid chains T are detected, which contributes to accurate detection.

The apparatus for nucleic acid separation which is covered by an embodiment of the present invention is designed to accomplish all of the above-mentioned steps 1 to 4 automatically. To be specific, it includes at least a fluid channel packed therein with a porous carrier having cation exchangeable groups attached thereto and a section configured to supply the fluid channel with a solution containing capturing chains modified with functional groups having positive charges. Consequently, the apparatus for nucleic acid separation performs automatically the step of immobilizing the capturing chains to the porous carrier through ion exchange bonding. Also, the apparatus for nucleic acid separation additionally has a section configured to supply the fluid channel with a sample solution and a solution containing detecting chains, so that it performs the above-mentioned steps 1 to 4 automatically to separate and detect the target nucleic acid.

The foregoing is concerned with the method for separating nucleic acids by means of the micro fluid channel 3 packed with the carrier for nucleic acid separation. However, the step of immobilizing the capturing chains to the surface of the porous carrier for nucleic acid separation may be accomplished in a micro tube (test tube). In this case, the tube or chip is provided with filters that hold the carrier for nucleic acid separation so that a bed of the carrier is formed. Thus there is obtained a column for nucleic acid separation which functions in the same way as the micro fluid channel 3.

The carrier for nucleic acid separation is not limited to beads. It may be one which has any structure of micro- or nano-channels or interstices. The micro beads should preferably be smaller than 1 mm in diameter so that they are readily packed into the fluid channel.

Example 1

1. Preparation of Micro Fluid Channel Packed with Carrier for Nucleic Acid Separation This example is intended to prepare a micro fluid channel packed with porous beads ("POROS 20S" from Applied Biosystems) whose surface is capable of cation exchange. These porous beads are perfusion chromatography particles having through pores and diffusive pores as mentioned above. They have sulfoethyl groups thereon which exhibit high cation exchangeability. They find use in ion exchange chromatography for concentration and separation of trace components.

The first step was to make ready a microchip (30 mm×70 mm×1.9 mm thick) of heat-resistant glass which is provided with a fluid channel having a square cross section (500 μm×500 μm) and a length of 60 mm. Both ends of the channel are connected to holes that open in the upper surface of the chip. The holes function respectively as the inlet and outlet of the channel.

The micro chip was mounted on a holder. The holder has threads so that tubes for solution feeding are fixed to the inlet and outlet of the microchip by means of ferrules and nuts. The ferrule at the downstream side is fitted with a filter having a pore diameter of 10 μm. The channel was packed with the porous beads fed from the upstream side, so that the porous beads form a 40-mm long bed, with one end thereof trapped by the filter.

Example 2

2. Measurement of Pressure in Fluid Channel

The micro fluid channel prepared in Example 1 was examined to see how pressure in it changes with flow rate.

For comparison, the same procedure as above was repeated by using the micro fluid channel disclosed in Patent Document 3 mentioned above. The micro fluid channel for comparison was packed with polystyrene beads (6 μm in diameter) having the poly(dT) sequence bonded thereto. The beads constitute a 2-mm long bed. In the downstream region was formed a 40-mm long bed packed with porous beads ("POROS S20S"). The bed of the polystyrene beads corresponds to the "hybrid forming section" and the bed of the porous beads correspond to the "solution supply accelerating section", both disclosed in Patent Document 3. The liquid phase for fluid flow was pure water.

Figure 5:
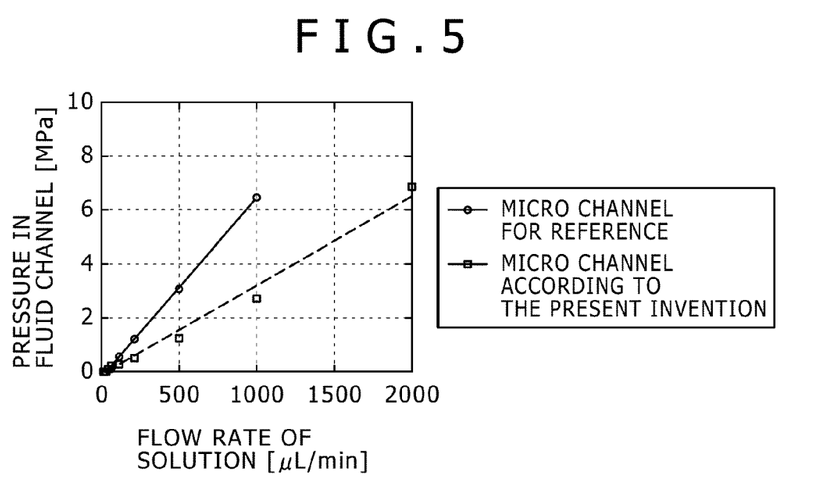
FIG. 5 is a diagram showing the results of measurement of the internal pressure in the channel (Example 2)

The pressure measurement gave the result shown in FIG. 5. The flow rate was varied from 0 to 2000 μl/min.

It is noted from FIG. 5 that the micro fluid channel for comparison caused the internal pressure to exceed 3 MPa and 6 MPa at the flow rate of 500 μl/min and 1000 μl/min, respectively. Moreover, the internal pressure exceeded 8 MPa at the flow rate of 2000 μl/min; it was high enough to cause leakage from the inlet, making pressure measurement impossible. By contrast, the micro fluid channel prepared in Example 1 experienced pressure increase less than one half that in the micro fluid channel for comparison.

Example 3

3. Immobilization of Capturing Chains to the Surface of Porous Carrier by Ion Exchange Bonding The result in Example 2 suggests that the micro fluid channel permits a high flow rate even though the bed is composed of porous beads alone. So, Example 3 was intended to separate nucleic acids only by using the bed of porous beads, while omitting the bed of existing polystyrene beads having poly(dT) sequence attached thereto. To this end, an attempt was made to immobilize the capturing chains onto the porous beads packed into the micro fluid channel.

<Synthesis of Capturing Chains>

The capturing chains were prepared by synthesizing $NH_2$-poly(dT)50-Cy3, which is a single-strand DNA (50 bases) of poly(dT) sequence having the 5' end modified with an amino group ($-NH_2$) and the 3' end labeled with Cy3 (cyanine 3). This single-strand DNA will be referred to as "capturing chain DNA" hereinafter. The capturing chain DNA was dissolved in an aqueous solution of 0.3 M sodium chloride containing 0.2 DS (sodium dodecyl sulfate) such that the resulting solution has a concentration of 5 μM.

<Immobilization of Capturing Chains Through Ion Exchange Bonding—Part 1>

The porous beads constituting the bed of the micro fluid channel were conditioned with an aqueous solution of 0.3 M sodium chloride containing SDS which was passed through the channel. Then, the porous beads were treated with 250 μl of the solution of capturing chain DNA and washed with 2 ml of aqueous solution of 0.3 M sodium chloride containing SDS.

After conditioning and cleaning, the intensity of fluorescence emitted from the bed was measured. (The fluorescence has a wavelength of 570 nm which corresponds to the fluorescence peak of Cy3.) No change was observed in the intensity of fluorescence. This result indicates that no ion exchange bonding occurred between the amino group at the 5' end of the capturing chain DNA and the sulfoethyl group on the bead surface, which means that the capturing chain DNA is not immobilized onto the bead surface. This is because the solution of the capturing chain DNA was prepared from an aqueous solution of 0.3 M sodium chloride containing SDS which has an excessively high concentration. Such a solution seems to impede ion exchange reaction between the amino group at the 5' end of the capturing chain DNA and the sulfoethyl group on the bead surface.

<Immobilization of Capturing Chains Through Ion Exchange Bonding—Part 2>

To cope with this situation, pure water was used to prepare the capturing chains DNA and perform the ion exchange reaction between the amino group at the 5' end of the capturing chain DNA and the sulfoethyl group on the bead surface.

The porous beads constituting the bed of the micro fluid channel were conditioned with pure water and then treated with 250 μl of aqueous solution containing 5 μM of the capturing chain DNA and finally washed twice with 2 ml of pure water. Further, the porous beads were treated with 2 ml of aqueous solution of 0.3 M sodium chloride containing SDS which was passed through three times for liquid phase replacement and washing.

Figure 6:
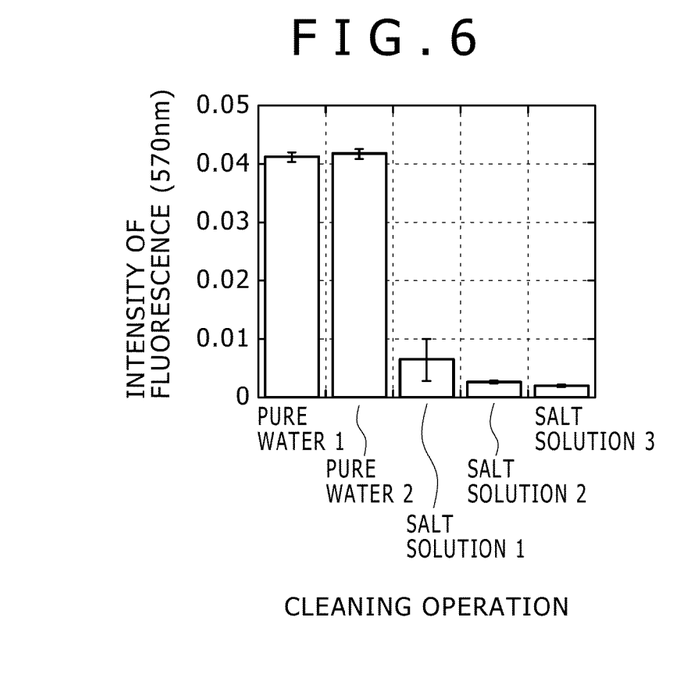
FIG. 6 is a diagraph showing the results of measurement of the intensity of fluorescence emitted from the bed due to immobilization of capturing chain DNA through ion exchange (Example 3)

After each step of cleaning, the intensity of fluorescence emitted from the bed was measured. The results are shown in FIG. 6. (The fluorescence has a wavelength of 570 nm which corresponds to the fluorescence peak of Cy3.)

It is noted that the bed emits fluorescence due to Cy3 if it is washed twice with pure water after passage of the solution of capturing chain DNA. See "pure water 1" and "pure water 2" in FIG. 6. This suggests that the capturing DNA firmly bonds to the bead surface.

It is also noted that the intensity of fluorescence emitted from the bed remarkably decreases in the case where washing with pure water is followed by replacement of the liquid phase by the solution of 0.3 M sodium chloride containing SDS. (See "salt solution 1" to "salt solution 3" in FIG. 6.) Probably, this is because the high concentration of the solution of 0.3 M sodium chloride containing SDS brings about dissociation of the ion exchange bonding between the sulfoethyl group on the bead surface and the amino group at the 5' end of the capturing chain DNA.

The foregoing results suggest that the capturing chains can be immobilized onto the bead surface if the ion exchange reaction between the sulfoethyl group on the bead surface and the amino group at the 5' end of the capturing chain DNA is carried out in pure water which permits the ion exchange reaction to continue.

<Determination of the Amount of Nonspecific Adsorption of Capturing Chains>

For the purpose of comparison, porous beads ("POROS BA" from Applied Biosystems) having no cation exchangeable groups on the bead surface were used to examine the non-specific adsorption of the capturing chain DNA to the surface of the porous carrier. The porous beads incapable of cation exchange do not bring about the ion exchange reaction with the amino group at the 5' end of the capturing chain DNA but permits the capturing chain DNA to attach itself to the bead surface only through nonspecific adsorption.

The procedure explained above in Example 1 was used to prepare the micro fluid channel for comparison which is packed with porous beads incapable of cation exchange. The capturing chain DNA was dissolved in an aqueous solution of 0.3 M sodium chloride containing SDS such that the resulting solution has a concentration of 5 μM.

The micro fluid channel for comparison was treated for conditioning with aqueous solution of 0.3 M sodium chloride containing SDS, with its temperature kept at 50° C. It was fed with 250 μl of solution containing capturing chain DNA and then washed with 2 ml of aqueous solution of 0.3 M sodium chloride containing SDS. After conditioning and washing, the intensity of fluorescence emitted from the bed was measured through a fluorescence filter set for Cy3.

The filter set passes fluorescence with wavelengths ranging from 567 nm to 625 nm. The result of measurement is shown in FIG. 7.

Figure 7:
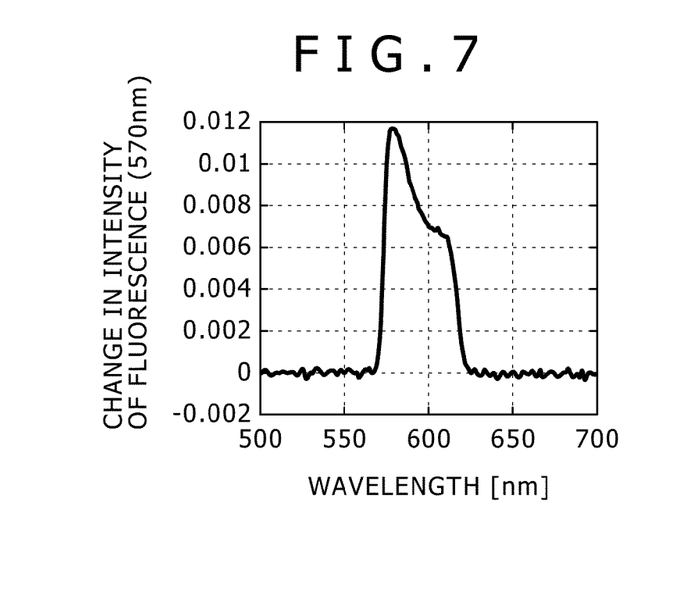
FIG. 7 is a diagram showing the results of measurement of the intensity of fluorescence emitted from the bed due to nonspecific adsorption of capturing chains (Example 3)

It is noted from FIG. 7 that the fluorescence due to Cy3 has a significant peak at 570 nm. This suggests that the capturing chain DNA underwent nonspecific adsorption to the surface of the porous beads.

The micro fluid channel for comparison causes the capturing chain DNA to suffer nonspecific adsorption even after washing with aqueous solution of 0.3 M sodium chloride containing SDS. By contrast, the porous beads capable of cation exchange prevents the capturing chain DNA from bonding to the bead surface as the result of the liquid phase being replaced by solution of 0.3 M sodium chloride containing SDS. (See "salt solution 1" to "salt solution 3" in FIG. 6.) This proves that the binding of the capturing chain DNA to the surface of the porous beads capable of cation exchange is not due to nonspecific adsorption but due to ion exchange bonding between the sulfoethyl group on the bead surface and the amino group at the 5' end of the capturing chain DNA.

Example 4

4. Detection of Target Nucleic Acid Chains with the Help of Porous Carrier on which Capturing Chains are Immobilized by Ion Exchange Bonding Example 3 revealed that the liquid phase replaced by aqueous solution of 0.3 M sodium chloride containing SDS brings about dissociation of the ion exchange bonding between the sulfoethyl group on the bead surface and the amino group at the 5' end of the capturing chain DNA. (See "salt solution 1" to "salt solution 3" in FIG. 6.) Thus, there is the possibility that the capturing chains dissociate from the surface of the porous carrier, thereby preventing separation of target nucleic acid chains, if hybridization of capturing chains and target nucleic acid chains is carried out in an aqueous solution of 0.3 M sodium chloride containing SDS. This example is intended to cope with this situation by immobilizing the capturing chains in pure water and allowing the hybridization reaction between capturing chains and target nucleic acid chains to take place rapidly in an aqueous solution of 0.3 M sodium chloride containing SDS, so that hybridization of capturing chains and target nucleic acid chains takes place before the capturing chains dissociate from the carrier surface, and the target nucleic acid chains are separated.

<Preparation of Carrier for Nucleic Acid Separation and Micro Fluid Channel>

The porous beads constituting the bed of the micro fluid channel were conditioned with pure water and then treated with 250 μl of aqueous solution containing 5 μM of the capturing chain DNA and finally washed with 2 ml of pure water. After conditioning and washing, the intensity of fluorescence was measured. The increased intensity of fluorescence indicates that the capturing chain DNA has been immobilized onto the surface of the porous beads.

<Synthesis of Target Nucleic Acid Chains>

The following two kinds of target nucleic acid chains were synthesized.

ssDNA (21 bases) of poly(dA) sequence labeled with Cy3, which is designated as Cy3-poly(dA)21.

ssDNA (21 bases) of poly(dT) sequence labeled with Cy3, which is designated as Cy3-poly(dT)21.

The former has a base sequence complementary to the capturing chain DNA ($NH_2$-poly(dT)50-Cy3). Cy3-poly(dA)21 and Cy3-poly(dT)21 will be referred to as target DNA and non-target DNA, respectively, hereinafter. Each of them was dissolved in an aqueous solution of 0.3 M sodium chloride containing SDS such that the resulting solution has a concentration of 5 μM.

<Separation of Target Nucleic Acid Chains>

The micro fluid channel was treated for conditioning with 250 μl of nontarget DNA solution and then washed for the first time with 2 ml of aqueous solution of 0.3 M sodium chloride containing SDS. After conditioning and washing, the intensity of fluorescence emitted from the bed was measured.

Subsequently, the micro fluid channel was treated with 250 μl of target DNA solution and then washed for the second time with 2 ml of aqueous solution of 0.3 M sodium chloride containing SDS. The intensity of fluorescence emitted from the bed was measured after the first washing and the second washing.

Figure 8:
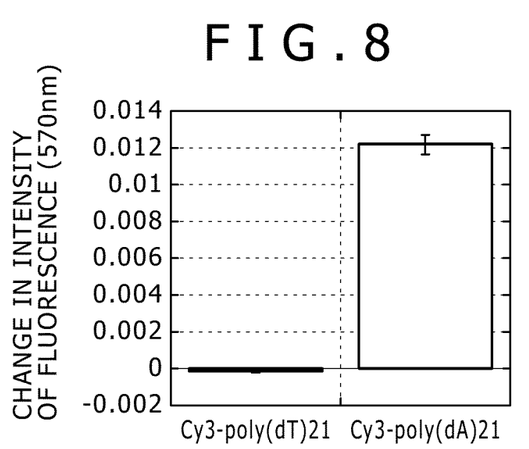
FIG. 8 is a diagram showing the results of measurement of the intensity of fluorescence of emitted from the bed due to separation of nucleic acid chains (Example 4)

The result of measurement is shown in FIG. 8. Incidentally, the intensity of fluorescence was measured at 570 nm, which is the peak due to Cy3.

It is noted that the intensity of fluorescence remained unchanged after conditioning and washing (for the first time) in the case where the micro fluid channel was treated with the solution of nontarget DNA (Cy3-poly(dT)21) which is not complementary to the capturing chain DNA. This suggests that hybridization did not occur between the capturing chain DNA and the nontarget DNA and the nontarget DNA did not experience nonspecific adsorption to the bead surface.

On the other hand, the target DNA (Cy3-poly(dA)21), which is complementary to the capturing chain DNA, showed a remarkable increase in the intensity of fluorescence. This indicates that hybridization occurred between the capturing chain DNA and the target DNA.

Example 5

5. Detection of Target Nucleic Acid Chains with the Help of Porous Carrier Having Capturing Chains Immobilized by Covalent Bonding The result of Example 4 suggests that the target nucleic acid chains can be hybridized to the capturing chains and separated with the help of hybridization between the capturing chains and the target nucleic acid chains so long as the capturing chains remain bonding to the surface of the carrier. This example is intended to separate the target nucleic acid chains in a more stable manner by causing the capturing chains to bind to the surface of the carrier through ion exchange reaction and further through covalent bonding.
<Preparation of Carrier for Nucleic Acid Separation and Micro Fluid Channel>

The capturing chain DNA was attached by ion exchange bonding to the bead surface in the same way as in Example 4, and then it was immobilized by covalent bonding by condensation accompanied by removal of ethanol. The capturing chain DNA used in this example is single-strand DNA (50 bases) of poly(T) sequence which is not labeled with Cy3. It is designated as $NH_2$-poly(dT)50.
<Separation of Target Nucleic Acid Chains>

The porous beads constituting the bed of the micro fluid channel were conditioned with an aqueous solution of 0.3 M sodium chloride containing SDS which was passed through the channel. Then, the porous beads were treated with 250 µl of solution of the target DNA (Cy3-poly(dA)21) and washed with 2 ml of aqueous solution of 0.3 M sodium chloride containing SDS. After conditioning and washing, the intensity of fluorescence emitted from the bed was measured.

Figure 9:
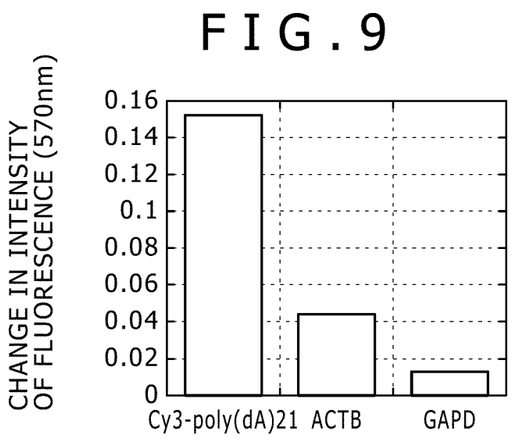
FIG. 9 is a diagram showing the results of measurement of the intensity of fluorescence emitted from the bed due to separation of nucleic acid chains (Examples 5 and 6).

The result of measurement is shown in FIG. 9 as marked with "Cy3-poly(dA)21." The intensity of fluorescence has a peak due to Cy3 at 570 nm. Incidentally, the symbols "ACTB" and "GAPD" in FIG. 9 will be explained later.

As shown in FIG. 9, the intensity of fluorescence remarkably increases after conditioning and washing. This suggests the occurrence of hybridization between capturing chain DNA and target DNA.

Example 6

6. Detection of mRNA

This example is intended to separate a specific mRNA as the target nucleic acid chains from total RNA extracted from cultured cells by using the carrier for nucleic acid separation and the micro fluid channel, both prepared in Example 5, and to detect the separated mRNA by the method of forming sandwich hybrids.
<Preparation of Total RNA>

Total RNA was extracted from cultured HeLa cells by using the total RNA extraction kit (RNeasy protect mini kit, Qiagen). The extracted total RNA (5 µg) was dissolved in 350 µl of aqueous solution of 0.3 M sodium chloride containing SDS. Thus there was obtained a sample solution.
<Synthesis of Detecting Chains>

The mRNA as the target nucleic acid chains is β-actin (ACTB) mRNA and glyceroaldehyde-3-phosphoric acid dehydrogenase (GAPD) mRNA. A base sequence with a length of 21 bases was selected from the sequence in the neighborhood of poly(A) tail of each mRNA. There were synthesized the detecting chains (with 21 bases) with a base sequence complementary to the selected base sequence. The detecting chains had the 5' end modified with Cy3. Table 1 shows the base sequence of the detecting chains corresponding to ACTB mRNA and GAPD mRNA. Each species of the detecting chains was dissolved in aqueous solution of 0.3 M sodium chloride containing SDS such that the resulting solution has a concentration of 5 µM.

TABLE 1

| ACTB mRNA | 5'-AAGGTGTGCACTTTTATTCAA-3' |
|---|---|
| GAPD mRNA | 5'-TACTTTATTGATGGTACATGA-3' |

<Detection of Target Nucleic Acid Chains by Sandwich-Hybrid Method>

The porous beads constituting the bed of the micro fluid channel were conditioned with an aqueous solution of 0.3 M sodium chloride containing SDS which was passed through the channel. Then, the porous beads were treated with the sample solution and washed with 700 µl of aqueous solution of 0.3 M sodium chloride containing SDS. Further, the porous beads were treated with the detecting chain solution which was passed thought the micro fluid channel and then washed with 2 ml of aqueous solution of 0.3 M sodium chloride containing SDS. After passage of the sample solution, the intensity of fluorescence emitted from the washed bed was measured. After passage of the detecting chain solution, the intensity of fluorescence emitted from the washed bed was measured.

The measured intensity of fluorescence is shown in FIG. 9, which is marked with "ACTB" and "GAPD". Incidentally, the intensity of fluorescence was measured at 570 nm, which is the peak due to Cy3.

It is noted that the intensity of fluorescence increased for both ACTB and GAPD. This suggests that the capturing chain DNA having poly(dT) sequence (which is immobilized onto the bead surface) and the poly(A) tail of mRNA in total RNA form the hybrid, so that the mRNA is captured onto the beads, and the detecting chains form the second hybrid with ACTB mRNA or GAPD mRNA in the captured mRNA.

The carrier for nucleic acid separation according to the above preferred embodiments of the present invention permits the hybridization of nucleic acids to be performed at a high flow rate without pressure increase in the fluid channel. Therefore, the present invention contributes to rapid separation of nucleic acids and efficient analysis of nucleic acids.

The present application contains subject matter related to that disclosed in Japanese Priority Patent Application JP 2008-120166, filed in the Japan Patent Office on May 2, 2008, the entire content of which is hereby incorporated by reference.

It should be understood by those skilled in the art that various modifications, combinations, sub-combinations and alterations may occur depending on design requirements and other factors insofar as they are within the scope of the appended claims or the equivalents thereof.

What is claimed is:

1. A carrier for nucleic acid separation comprising:
   a microchip having a microfluid channel running therethrough;
   a porous microbead disposed within the microfluid channel, the porous microbead having at least one cation-exchangeable group comprising a sulfoethyl group attached to a surface of the porous microbead; and
   at least one capturing chain immobilized on to the surface of the porous microbead through an ion exchange bond with the at least one cation-exchangeable group, wherein the at least one capturing chain has a nucleic acid base sequence complementary to a target nucleic acid chain sequence and the at least one capturing chain is modified with a functional group comprising an amino group.

2. The carrier for nucleic acid separation of claim 1, wherein the microfluid channel is packed with a plurality of the porous microbead.

3. The carrier for nucleic acid separation of claim 1, wherein the porous microbead further comprises a plurality of through pores adapted to permit a solution to pass rapidly therethrough and a plurality of diffusive pores adapted to permit a solute of the solution to diffuse into the plurality of diffusive pores.

4. A method for producing a carrier for nucleic acid separation, the method comprising:
   providing a microchip having a microfluid channel running therethrough;
   placing a plurality of porous microbeads within the microfluid channel, each porous microbead having at least one cation-exchangeable group comprising a sulfoethyl group attached to a surface of the porous microbead;
   modifying the porous microbead by contacting the surface of the porous microbead with at least one capturing chain in pure water resulting in a reaction of the at least one capturing chain with the at least one cation-exchangeable group forming an immobilizing bond between the at least one capturing chain and the at least one cation-exchangeable group, the at least one capturing chain having a nucleic acid base sequence complementary to a target nucleic acid chain sequence, and the at least one capturing chain modified with a functional group comprising an amino group.

5. The method for producing a carrier for nucleic acid separation as defined in claim 4, wherein contacting the surface of the porous microbead with the at least one capturing chain comprises passing a solution containing the at least one capturing chain through the porous microbead.

6. A method for producing a carrier for nucleic acid separation, the method comprising:
   providing a microchip having a microfluid channel running therethrough;
   placing a plurality of porous microbeads within the microfluid channel, each porous microbead having at least one cation-exchangeable group comprising a sulfoethyl group attached to a surface of the porous microbead;
   modifying the porous microbead by contacting the surface of the porous microbead with at least one capturing chain in pure water resulting in a reaction of the at least one capturing chain with the at least one cation-exchangeable group, the at least one capturing chain having a nucleic acid base sequence complementary to a target nucleic acid chain sequence, the at least one capturing chain modified with a functional group comprising an amino group.

7. A method for performing nucleic acid separation, the method comprising:
   providing a microchip having a microfluid channel running therethrough;
   providing a plurality of porous microbeads within the microfluid channel, each porous microbead having at least one cation-exchangeable group bonded to at least one capturing chain on a surface of the porous microbead, the at least one cation-exchangeable group comprising a sulfoethyl group, the at least one capturing chain having a nucleic acid base sequence complementary to a target nucleic acid chain sequence, the at least one capturing chain modified with a functional group comprising an amino group; and
   passing at least one target nucleic acid chain corresponding to the target nucleic acid chain sequence through the porous microbead resulting in hybridization of the at least one capturing chain and the at least one target nucleic acid chain.

8. A method for performing nucleic acid separation, the method comprising:
   providing a microchip having a microfluid channel running therethrough;
   providing a plurality of porous microbeads within the microfluid channel, each porous microbead having a plurality of through pores adapted to permit a solution to pass rapidly therethrough and a plurality of diffusive pores adapted to permit a solute of the solution to diffuse into the plurality of diffusive pores, the porous microbead having at least one capturing chain attached to a surface of the porous microbead, the at least one capturing chain having a nucleic acid base sequence complementary to a target nucleic acid chain sequence; and
   passing at least one target nucleic acid chain corresponding to the target nucleic acid chain sequence through the porous microbead resulting in hybridization of the at least one capturing chain and the at least one target nucleic acid chain.

* * * * *